(12) United States Patent
Purkayastha et al.

(10) Patent No.: US 11,161,804 B2
(45) Date of Patent: Nov. 2, 2021

(54) UNSYMMETRICALLY SUBSTITUTED DICARBOXYLIC ACID DIAMIDO AMMONIUM SALTS AND THEIR USE FOR GAS HYDRATE ANTI-AGGLOMERATION

(71) Applicant: Clariant International, Ltd., Muttenz (CH)

(72) Inventors: Nirupam Purkayastha, Bad Soden (DE); Zachary Thomas Ward, Spring, TX (US); Fabian Schneider, Eppelheim (DE); Dirk Leinweber, Kelkheim (DE); Matthias Krull, Harxheim (DE); Jonathan James Wylde, The Woodlands, TX (US)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 16/155,105

(22) Filed: Oct. 9, 2018

(65) Prior Publication Data
US 2020/0109107 A1   Apr. 9, 2020

(51) Int. Cl.
*C07C 233/36* (2006.01)
*C07D 295/13* (2006.01)

(52) U.S. Cl.
CPC .......... *C07C 233/36* (2013.01); *C07D 295/13* (2013.01)

(58) Field of Classification Search
None
See application file for complete search history.

(56) References Cited

U.S. PATENT DOCUMENTS

| | | | |
|---|---|---|---|
| 4,915,176 | A | 4/1990 | Sugier |
| 4,973,775 | A | 11/1990 | Sugier |
| 5,244,878 | A | 9/1993 | Sugier |
| 5,460,728 | A | 10/1995 | Klomp |
| 5,648,575 | A | 7/1997 | Klomp |
| 5,879,561 | A | 3/1999 | Klomp |
| 6,015,929 | A | 1/2000 | Rabeony |
| 6,369,004 | B1 | 4/2002 | Klug |
| 6,596,911 | B2 | 7/2003 | Przybylinski |
| 7,381,689 | B2 | 6/2008 | Panchalingam |
| 2004/0163306 | A1 | 8/2004 | Dahlmann |
| 2004/0167040 | A1 | 8/2004 | Dahlmann |
| 2005/0081432 | A1 | 4/2005 | Panchalingam |
| 2005/0101495 | A1 | 5/2005 | Dahlmann |
| 2006/0237691 | A1 | 10/2006 | Meier |
| 2007/0079963 | A1 | 4/2007 | Yang |
| 2009/0042749 | A1 | 2/2009 | Meier |
| 2009/0173663 | A1 | 7/2009 | Leinweber |
| 2014/0091262 | A1 | 4/2014 | Webber |
| 2016/0122619 | A1* | 5/2016 | Lucente-Schultz ............ C07C 237/10 507/90 |
| 2016/0186039 | A1 | 6/2016 | Owsik |
| 2018/0333339 | A1 | 11/2018 | Hamersky |

(Continued)

FOREIGN PATENT DOCUMENTS

| | | |
|---|---|---|
| CN | 101906293 | 12/2010 |
| CN | 105733539 | 7/2016 |
| EP | 0651049 | 5/1995 |

(Continued)

OTHER PUBLICATIONS

International Search Report and Written Opinion for App. No. PCT/EP2020/084717, dated Mar. 3, 2021, 14 pages.

(Continued)

*Primary Examiner* — Jeffrey D Washville
(74) *Attorney, Agent, or Firm* — Tod A. Waldrop

(57) ABSTRACT

The instant invention concerns a gas hydrate inhibitor comprising an N alkyl N' (N",N"-dialkylammoniumalkyl)dicarboxylic acid diamide salt represented by the formula (I)

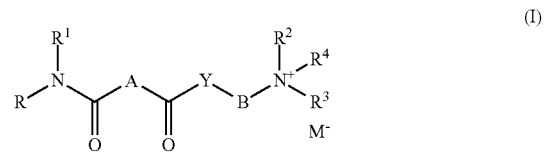

wherein

R is an alkyl or alkenyl group having from 8 to 22 carbon atoms, $R^1$ is hydrogen, a $C_1$- to $C_{22}$ alkyl group or a $C_3$- to $C_{22}$ alkenyl group, $R^2$ and $R^3$ are each independently an alkyl group containing 1 to 10 carbon atoms or together form an optionally substituted ring having 5 to 10 ring atoms, wherein the ring may carry up to 3 substituents, R4 is hydrogen, A is an optionally substituted hydrocarbyl group containing from 1 to 18 carbon atoms, B is an alkylene group having from 2 to 6 carbon atoms, Y is $NR^5$, $R^5$ is hydrogen, a $C_1$- to $C_{22}$ alkyl group or a $C_3$- to $C_{22}$ alkenyl group, and M– is an anion, a process for producing a compound according to formula (I), the use of an N alkyl N'—(N",N"-dialkylammoniumalkyl)dicarboxylic acid diamide salt of the formula (I) as an anti-agglomerant for gas hydrates, and a method for inhibiting the agglomeration of gas hydrates which comprises the addition of an N alkyl N' (N",N"dialkylammmoniumalkyl) dicarboxylic acid diamide salt of the formula (I) to a fluid containing gas and water.

24 Claims, No Drawings

(56) References Cited

U.S. PATENT DOCUMENTS

| | | |
|---|---|---|
| 2018/0346790 A1 | 12/2018 | Pou |
| 2018/0346791 A1 | 12/2018 | Bartels |

FOREIGN PATENT DOCUMENTS

| | | |
|---|---|---|
| GB | 2349889 | 11/2000 |
| WO | 2002066785 | 8/2002 |
| WO | 2005042675 | 5/2005 |
| WO | 2006072083 | 7/2006 |
| WO | 2012082815 | 6/2012 |
| WO | 2012102916 | 8/2012 |
| WO | 2013089802 | 6/2013 |
| WO | 2016069987 | 5/2016 |
| WO | 2017089724 | 6/2017 |
| WO | 2017184115 | 10/2017 |
| WO | 2017223306 | 12/2017 |
| WO | 2018115186 | 6/2018 |
| WO | 2019015828 | 1/2019 |

OTHER PUBLICATIONS

International Search Report and Written Opinion for App. No. PCT/EP2020/084721, dated Mar. 4, 2021, 16 pages.
International Search Report and Written Opinion for App. No. PCT/EP2020/084724, dated Mar. 4, 2021, 16 pages.
International Search Report for App. No. PCT/EP2019/074182 dated Dec. 6, 2019, 4 pages.
Machine translation of CN101906293, Aug. 12, 2010, 24 pages.
Whitmore et al., "Basically Substituted Aliphatic Nitriles and their Catalytic Reduction to Amines", Jornal of American Chemical Society, vol. 66, May 1944, pp. 725-731.
M. Sun, et al., J. Colloid Interf. Sci., 402 (2013), pp. 312-319.

* cited by examiner

UNSYMMETRICALLY SUBSTITUTED DICARBOXYLIC ACID DIAMIDO AMMONIUM SALTS AND THEIR USE FOR GAS HYDRATE ANTI-AGGLOMERATION

The present invention relates to a low dosage gas hydrate inhibitor which comprises at least one unsymmetrically substituted dicarboxylic acid diamido ammonium salt and a method for preventing, inhibiting, or otherwise modifying the agglomeration of gas hydrates by adding an effective amount of the inhibitor to a multiphase mixture comprising water, gas and, in some cases, condensate, black oil and/or drilling mud. The inhibitor effects improved anti-agglomeration of gas hydrates in petroleum fluids containing varying amounts of water/brine, crude oil/condensate, and natural gas as for example in crude hydrocarbon streams under conditions prone to the formation of gas hydrates. It is obtainable from renewable materials and has good biodegradability.

A number of hydrocarbons, especially low molecular weight hydrocarbons with 1 to 6 carbon atoms are known to form hydrates. Hydrates may form in conjunction with water present in the system under a variety of conditions—particularly at the combination of lower temperature and higher pressure. In the oil and gas industry such conditions often prevail in formation fluids and in equipment containing natural gas. Usually gas hydrates are solids that are essentially insoluble in the fluid itself. Any solids, including hydrates, present in a formation or natural gas fluid are problematic for production, handling and transport of these fluids. The solid hydrates may cause plugging and/or blockage of pipelines, transfer lines and other conduits, of valves and/or safety devices and/or other equipment. This may result in shutdown, lost oil production, pipeline damage, risk of explosion or unintended release of hydrocarbons into the environment either on-land or off-shore. Therefore it poses a safety hazard to field workers and the public. The damage resulting from a blockage can be very costly from an equipment repair standpoint, as well as from the loss of production, and finally the resultant environmental impact. Accordingly, gas hydrates are of substantial interest as well as concern to many industries, particularly the petroleum and natural gas industry.

Gas hydrates are clathrates, and are also referred to as inclusion compounds. Clathrates are cage structures formed between a host molecule and a guest molecule. A gas hydrate generally is composed of crystals formed by water host molecules surrounding the hydrocarbon guest molecules. The smaller and lower-boiling hydrocarbon molecules, particularly $C_1$- (methane) to $C_4$ hydrocarbons and their mixtures, are especially problematic because their hydrate or clathrate crystals are easy to form. For instance, it is possible for ethane to form hydrates at as high as 4° C. at a pressure of about 1 MPa. If the pressure is about 3 MPa, ethane hydrates can form at as high a temperature as 14° C. Even certain non-hydrocarbons such as carbon dioxide, nitrogen and hydrogen sulfide are known to form hydrates under certain conditions. Thus, when the appropriate conditions are present, hydrates can be easily formed for example during the transportation of oil and gas in pipelines.

Modern oil and gas technologies tend to operate under increasingly severe conditions. For example, during the course of drilling operations as well as during oil recovery and production, high pumping speed, high pressure in the pipelines, extended length of pipelines, and low temperature of the oil and gas flowing through the pipelines, for example in subsea operations are applied. This increases the frequency of formation of gas hydrates.

There are two basic techniques to overcome or control the gas hydrate problems, namely thermodynamic and kinetic. For the thermodynamic approach a number of methods have been reported, including water removal, increasing temperature, decreasing pressure, addition of "antifreeze" to the fluid and/or a combination of these (known in the industry as Thermodynamic Hydrate Inhibitors and abbreviated THI). The kinetic approach generally attempts to inhibit and/or retard initial gas hydrate crystal nucleation and/or further crystal growth (known in the industry as a Kinetic Hydrate Inhibitor and abbreviated KHI). Thermodynamic and kinetic hydrate control methods may be used in conjunction.

The amount of chemical needed to prevent blockages varies widely depending upon the type of inhibitor employed. Thermodynamic hydrate inhibitors are substances that can reduce the temperature at which the hydrates form at a given pressure and water content. They are typically used at very high concentrations (regularly dosed as high as 50 wt.-% based on water content, with glycol often being used in amounts equal to the weight of water present in the system). Therefore, there is a substantial cost associated with the provision, transportation and storage of large quantities of these solvents. The use of kinetic hydrate inhibitors is a more cost-effective alternative as they generally require a dose of less than about 2 wt.-% based on the water content to inhibit the nucleation and/or growth of gas hydrates. Kinetic hydrate inhibitors are often also labeled Low Dosage Hydrate Inhibitors (abbreviated LDHI).

Besides the kinetic hydrate inhibitors (KHIs) there is a second general type of LDHIs, the so-called Anti-Agglomerants (abbreviated AA). While KHIs work by delaying the growth of gas hydrate crystals and may function as "antinucleators", AAs allow hydrates to form but prevent them from agglomerating and subsequently from accumulating into larger aggregates capable of causing plugs. Often AAs prevent the once formed smaller gas hydrate crystals to adhere to the pipe wall.

Kinetic efforts to control hydrates have included the use of different chemicals as inhibitors. Typically, KHIs are low molecular weight polymers that adsorb on gas hydrate crystal faces and interfere with the nucleation and growth of gas hydrate crystals. For instance, polymers with lactam rings (stemming e.g. from vinyl caprolactam) have been employed to control clathrate hydrates in fluid systems. Similarly, onium compounds with at least four carbon substituents are used to inhibit the plugging of conduits by gas hydrates. Unfortunately, there are several limitations that have been discovered with the use of KHIs such as subcooling limits, solubility problems based on temperature and salt content of the water, and chemical incompatibility with the system being treated.

Anti-agglomerants typically are surface active molecules (amphiphiles). When small gas hydrate crystals begin to form, AAs attach to them via their polar headgroup. This makes the surface hydrophobic, which mediates the capillary attraction between the crystals and water and fosters dispersion of the crystals in a liquid hydrocarbon phase. This results in a relatively stable and transportable hydrate slurry in a liquid hydrocarbon phase that can flow to the processing facility. AAs are usually added at dose rates of less than 0.5 wt.-% and up to 2.0 wt.-% based on the water phase.

Besides some polymeric substances and especially nitrogen-containing polymers many different monomeric substances have been described to work as anti-agglomerant.

Quaternary amine chemistry has been proven to be especially effective as anti-agglomerant for hydrate control. The best performing AAs are quaternary ammonium surfactants in which the ammonium headgroup has two or three butyl or pentyl groups attached to the quaternary nitrogen.

A variety of approaches to optimize the performance of anti-agglomerants by modifying the amphiphilic properties of anti-agglomerants in respect to the structure of hydrophilic and lipophilic groups and their balance have been made.

GB 2349889 discloses a method for inhibiting the formation, agglomeration and plugging of gas hydrates in a fluid containing hydrate forming constituents by adding to the hydrate forming fluids an additive comprising one or more amide compounds of molecular weight less than 1.000.

WO 2013/089802 discloses the use of beta-amino amide surfactants as anti-agglomerants to reduce or inhibit the formation of gas hydrates. The additives are obtainable by nucleophilic addition of dialkyl amine to acrylic acid and subsequent amidation of the carboxyl group with a fatty amine.

WO 2012/102916 discloses tertiary amine salts and their use as gas hydrate inhibitors in oil and gas production and transportation. These tertiary amine salts give very good separation from an emulsion, are economic and have reduced toxicity concerns.

WO 2016/069987 discloses low dosage hydrate inhibitors that can inhibit the formation of hydrate agglomerates and/or plugs. The hydrate inhibitors may be cationic ammonium surfactants having an ionizable secondary amine.

US 2004/163306 discloses quaternary trialkylammonium alkyl esters and quaternary trialkylammonium alkyl amides, optionally containing quaternary trialkylammonium alkyl imides, of dicarboxylic acids for inhibiting nucleation, growth and/or agglomeration of gas hydrates. This inhibitor is added to a multiphase mixture which consists of water, gas and in some cases condensate and has a tendency to form hydrates, or to a drilling mud which tends to form gas hydrates. Besides excellent action as gas hydrate inhibitors, they are alleged to show good biodegradability. However, the examples are limited to dialkylaminoalkylesters of alkenyl succinic anhydride respectively of ether dicarboxylic acids.

WO 2005/042675 discloses a method and an amide composition used therein for inhibiting, retarding, mitigating, reducing, controlling and/or delaying the formation of gas hydrates or agglomerates of gas hydrates. The disclosure encompasses the amides obtained by reaction of an N,N-dialkylaminoalkylamine with an ester or glyceride as for example a vegetable oil or tallow oil and subsequent reaction with a reactant selected from an alkyl halide, hydrogen peroxide and an acid.

WO 2017/223306 discloses an anti-agglomerant additive formulation comprising the reaction product of a (i) dicarboxylic acid reactant and (ii) a nitrogen containing compound having an oxygen or nitrogen atom capable of condensing with said hydrocarbyl substituted dicarboxylic acid, and further having at least one quaternizeable amino group, and (iii) a quaternizing agent for quaternization of the nitrogen containing compound.

However, due to their chemistry most of the anti-agglomerants are toxic and only a few of them are biodegradable. Many of the known anti-agglomerants show high potential for bioaccumulation. Due to their surface activity water quality and fluids separation upon application of quaternary ammonium surfactants are industrial-wide technical challenges, therefore thwarting its broad field implementation to replace conventional THI methods. Thus, it is desirable if new gas hydrate inhibitors were discovered which yield comparable or even improved results over known gas hydrate inhibitors. Improved AAs must reduce the agglomeration tendency of hydrates in conditions under which a hydrate may be formed. They should prevent gas hydrate agglomeration at least 10° C. and preferably 15° C. below the thermodynamic hydrate formation temperature, i.e. they have to allow a subcooling of 10° C., preferably 15° C. and more. Additionally they have to remain effective through long shut in periods (days to weeks or even months) at dose rates of about 0.5-3.0 wt.-%.

Furthermore, KHIs and even LDHIs are relatively expensive chemicals. Accordingly there is a constant strive for more efficient LDHIs which require lower dosage rates while maintaining effective hydrate inhibition and/or allowing for higher subcooling. Similarly there is an ambition for new synthetic routes for gas hydrate inhibitors having improved economics as well as an improved ecological footprint. In doing so the use of a high portion of renewable raw materials is desirable.

An additional technical limitation of most anti-agglomerants is that they require a hydrocarbon phase (e.g. oil or gas condensate) to disperse the gas hydrate crystals. Thus, their application is often restricted to fluid systems prone to hydrate formation with oil contents of at least 50 vol.-% and preferably of at least 60 vol.-% and vice versa to lower water-cuts. In general, the water-cut should be below 80 vol.-%, and especially with brine having low salinity it should be below 60 vol.-% and preferably below 50 vol.-% of the fluid to be treated as otherwise the crystals cannot be dispersed and/or the slurry may become too viscous for transport.

Accordingly, there is an ongoing need for compositions and methods that effectively prevent agglomeration of gas hydrates especially in oil and gas transportation and handling processes. Particularly there is the need for anti-agglomerants which need lower dosage rates to maintain effective hydrate inhibition. This need is especially strong for the treatment of fluids with higher water-cuts, particularly of greater than 50 vol.-%. Furthermore, the synthesis of gas hydrate inhibitors should have a favorable ecological footprint and should be based on a high portion of renewable raw materials. The still unsatisfactory biodegradability of known AAs is required to be improved.

Surprisingly it was found that salts of N-alkyl-N'—(N",N"-dialkylaminoalkyl)dicarboxylic acid diamides prevent gas hydrate agglomeration very effectively even with very low dosage rates. These salts are also advantageous at raised water-cuts. Additionally, the formation and/or agglomeration of hydrate crystals is delayed for a significant length of time and therefore prevents problems occurring during shut-in periods. The salts of N-alkyl-N'—(N",N"-dialkylaminoalkyl)dicarboxylic acid diamides according to the invention are obtainable from renewable materials; they can be produced with only little or even no side products (except water). Additionally they have a very good biodegradability profile.

Accordingly, in a first aspect of the invention there is provided a gas hydrate inhibitor comprising an N-alkyl-N'—(N",N"-dialkylammoniumalkyl)dicarboxylic acid diamide salt represented by the formula (I)

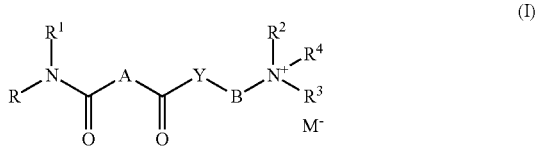

wherein
R is an alkyl or alkenyl group having from 8 to 22 carbon atoms,
$R^1$ is hydrogen, a $C_1$- to $C_{22}$ alkyl group or a $C_3$- to $C_{22}$ alkenyl group,
$R^2$ and $R^3$ are each independently an alkyl group containing 1 to 10 carbon atoms, or together form an optionally substituted ring having 5 to 10 ring atoms, wherein the ring may carry up to 3 substituents,
$R^4$ is hydrogen,
A is an optionally substituted hydrocarbyl group containing from 1 to 18 carbon atoms,
B is an alkylene group having from 2 to 6 carbon atoms,
Y is $NR^5$,
$R^5$ is hydrogen, a $C_1$- to $C_{22}$ alkyl group or a $C_3$- to $C_{22}$ alkenyl group, and
$M^-$ is an anion.

In a second aspect of the invention there is provided a process for producing a compound according to formula (I) wherein the process comprises:
i) the condensation of a dicarboxylic acid with a fatty amine to form a preferably cyclic imide intermediate,
ii) performing a ring opening reaction of the preferably cyclic imide intermediate with an N,N-dialkylaminoalkyl amine to form the N-alkyl-N'—(N'',N''-dialkylaminoalkyl)dicarboxylic acid diamide of formula (II),

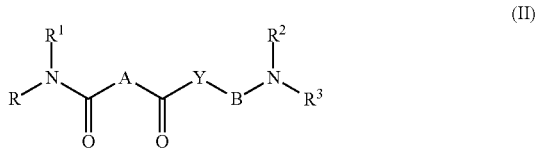

wherein
R is an alkyl or alkenyl group having from 8 to 22 carbon atoms,
$R^1$ is hydrogen, a $C_1$- to $C_{22}$ alkyl group or a $C_3$- to $C_{22}$ alkenyl group,
$R^2$ and $R^3$ are each independently an alkyl group containing 1 to 10 carbon atoms, or together form an optionally substituted ring having 5 to 10 ring atoms, wherein the ring may carry up to 3 substituents,
A is an optionally substituted hydrocarbyl group containing from 1 to 18 carbon atoms,
B is an alkylene group having from 2 to 6 carbon atoms,
Y is $NR^5$, and
$R^5$ is hydrogen, a $C_1$- to $C_{22}$ alkyl group or a $C_3$- to $C_{22}$ alkenyl group.
and
iii) reaction of the N-alkyl-N'—(N'',N''-dialkylaminoalkyl)dicarboxylic acid diamide (11) with an acid to form the N-alkyl-N'—(N'',N''-dialkylammoniumalkyl)dicarboxylic acid diamide salt of formula (I).

In a third aspect of the invention there is provided the use of an N-alkyl-N'—(N'',N''-dialkylammoniumalkyl)dicarboxylic acid diamide salt of the formula (I) according to the first aspect of the invention as an anti-agglomerant for gas hydrates.

In a fourth aspect of the invention there is provided a method for inhibiting the agglomeration of gas hydrates which comprises the addition of an N-alkyl-N'—(N'',N''-dialkylammmoniumalkyl)dicarboxylic acid diamide salt of the formula (I) according to the first aspect of the invention to a fluid containing gas and water.

In the context of this invention the terms hydrate, hydrocarbon hydrate, gas hydrate and clathrate all refer to solid hydrates of low molecular weight hydrocarbons and water and are used synonymously.

The compounds according to formulae I and II are an acid and its conjugated base and form an acid/base equilibrium. Consequently, in a preferred embodiment of the instant invention, the gas hydrate inhibitor comprises both an N-alkyl-N'—(N'',N''-dialkylammoniumalkyl)dicarboxylic acid diamide salt represented by the formula (I) and an N-alkyl-N'—(N'',N''-dialkylaminoalkyl)dicarboxylic acid diamide of the formula (II). In N-alkyl-N'—(N'',N''-dialkylammmoniumalkyl)dicarboxylic acid diamide salts (I) $R^4$ is present. In the N-alkyl-N'—(N'',N''-dialkylaminoalkyl)dicarboxylic acid diamides of formula (II) $R^4$ is absent.

The N-alkyl-N'—(N'',N''-dialkylaminoalkyl)dicarboxylic acid diamides of the formula (II) may be obtained by the condensation of a dicarboxylic acid with a fatty amine to give an intermediate amide and/or imide, followed by the reaction of the intermediate amide and/or imide with a N,N-dialkylaminoalkylamine. The salts of the formula (I) may be synthesized from the N-alkyl-N'—(N'',N''-dialkylaminoalkyl)dicarboxylic acid diamide (II) by reaction with an acid.

Dicarboxylic Acid

In a preferred embodiment A is the linking element in a dicarboxylic acid according to formula (III) or a derivative thereof.

HOOC-A-COOH (III)

wherein A is an optionally substituted hydrocarbyl group containing from 1 to 18 carbon atoms. Preferably A is an optionally substituted hydrocarbyl group comprising between 2 and 12 carbon atoms and especially preferred between 2 and 6 carbon atoms, as for example between 1 and 12 carbon atoms, or between 1 and 6 carbon atoms, or between 2 and 22 carbon atoms. Preferred substituents are hydroxyl groups. In a preferred embodiment A is a hydrocarbyl group consisting only of carbon and hydrogen, and A is not substituted.

In a first preferred embodiment the optionally substituted hydrocarbyl group A is an optionally substituted aliphatic group. Preferred aliphatic groups have 1 to 10 and especially preferred 2 to 6 carbon atoms as for example 1 to 6 carbon atoms or 2 to 10 carbon atoms. The aliphatic group A may be linear or branched. Preferably the optionally substituted aliphatic group A is linear. Preferred aliphatic groups A having two or more carbon atoms may be saturated or unsaturated. Preferably they are saturated. Substituents, if present, may be bound to any of the carbon atoms of the aliphatic group A but preferably only one substituent per carbon atom.

In a further preferred embodiment the optionally substituted hydrocarbyl group A is an optionally substituted aromatic group having 6 to 22 carbon atoms and preferably between 6 and 12 carbon atoms. The aromatic hydrocarbyl group A may be substituted by one or more alkyl residues with preferred alkyl residues having 1 to 4 carbon atoms.

Examples for suited alkyl substituents are methyl, ethyl, propyl and butyl groups. The carbon atom number of such alkyl residues is included in the total number of carbon atoms of the structural element A.

Examples for preferred dicarboxylic acids according to formula (III) as raw materials for the synthesis of N-alkyl-N'—(N",N"-dialkylaminoalkyl)dicarboxylic acid diamides (II) and their salts (I) are oxalic acid, malonic acid, succinic acid, glutaric acid, adipic acid, pimelic acid, malic acid, maleic acid, fumaric acid, tartronic acid, tartaric acid, azelaic acid, sebacic acid, 1,10-decanedioic acid, tetrahydrophthalic acid, phthalic acid, isophthalic acid and terephthalic acid.

Besides the dicarboxylic acids described above, their reactive derivatives are similarly suited for the synthesis of the N-alkyl-N'—(N",N"-dialkylaminoalkyl)dicarboxylic acid diamides (II) and their salts (I); sometimes they are even advantageous. Preferred reactive derivatives of the dicarboxylic acid according to formula (III) are dicarboxylic acid anhydrides, dicarboxylic acid halides and dicarboxylic acid esters with lower alcohols having 1 to 4 carbon atoms as for example methanol, ethanol, propanol, iso-propanol, butanol, isobutanol and tert.-butanol. Especially preferred reactive derivatives are anhydrides and diesters. Examples for particularly suitable dicarboxylic acid derivatives are maleic anhydride, succinic anhydride and phthalic anhydride.

Fatty Amine

Preferably in formulae (I) and (II) the structural element —$NRR^1$ is stemming from the reaction of a primary or a secondary fatty amine $HNRR^1$, wherein R and $R^1$ have the meanings given above, with a dicarboxylic acid (III) or its derivative.

In a preferred embodiment R is an alkyl or alkenyl group having from 10 to 18 carbon atoms especially preferred from 12 to 14 carbon atoms, as for example from 10 to 22, or from 10 to 14 carbon atoms, or from 8 to 18 carbon atoms, or from 8 to 14 carbon atoms, or from 12 to 22 carbon atoms, or from 12 to 18 carbon atoms. Especially preferred is a mixture consisting essentially of $C_{12}$ and $C_{14}$ alkyl respectively alkenyl residues. Here, essentially means that preferably at least 70 mol-%, more preferably at least 85 mol % and most preferred at least 90 mol-% of the alkyl and/or alkenyl residues have from 12 to 14 carbon atoms. Preferred alkyl residues R may be linear or branched. More preferably they are linear. Preferred alkenyl radicals may have or more C=C double bonds as for example one or two double bonds.

In a preferred embodiment $R^1$ is hydrogen or a $C_1$- to $C_6$ alkyl group as for example a methyl or ethyl group or a $C_3$- to $C_6$ alkenyl group. Especially preferred $R^1$ is hydrogen.

Examples for preferred amines are octylamine, nonylamine, decylamine, undecylamine, dodecylamine, tridecylamine, tetradecylamine, pentadecylamine, hexadecylamine, octadecylamine, behenylamine, oleylamine, N-methyl-octylamine, N-methyl-dodecylamine, N-methyl-tetradecylamine and their mixtures. Preferred mixtures of amines $NRR^1$ are based on renewable materials as for example on palm amine, coco amine, soya amine, rapeseed amine and tallow amine. Especially preferred are the primary amines (wherein $R^1$ is hydrogen) and their mixtures.

N,N-Dialkylaminoalkyleneamine

Preferably in formulae (I) and (II) the structural element —Y—B—$NR^2R^3$ is stemming from a N,N-dialkylaminoalkyleneamine having the structure (IV)

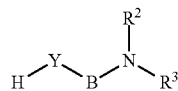

(IV)

wherein $R^2$ and $R^3$ are each independently an alkyl group containing 1 to 10 carbon atoms or together form an optionally substituted ring having 5 to 10 ring atoms, wherein the ring may carry up to 3 substituents, B is an alkylene group having from 2 to 6 carbon atoms, Y is $NR^5$, with $R^5$ being hydrogen, a $C_1$- to $C_{22}$ alkyl group or a $C_3$- to $C_{22}$ alkenyl group.

In a preferred embodiment $R^2$ and $R^3$ are each independently from another an alkyl group having 2 to 6 carbon atoms, more preferably having 3 to 5 carbon atoms and especially preferred having 3 or 4 carbon atoms, as for example having 1 to 6 carbon atoms, or having 1 to 5 carbon atoms, or having 1 to 4 carbon atoms, or having 2 to 10 carbon atoms, or having 2 to 5 carbon atoms, or having 2 to 4 carbon atoms, or having 3 to 10 carbon atoms, or having 3 to 6 carbon atoms. Examples for preferred alkyl residues are methyl, ethyl, propyl, iso-propyl, n-butyl, iso-butyl, tert.-butyl, the various isomers of pentyl, hexyl, heptyl, octyl, nonyl and decyl and their mixtures. Especially preferred are linear alkyl residues. $R^2$ and $R^3$ may be different or they may be the same. In a preferred embodiment $R^2$ and $R^3$ have 4 carbon atoms. In a further preferred embodiment $R^2$ and $R^3$ are linear alkyl residues. In a most preferred embodiment $R^2$ and $R^3$ both are linear $C_4$-alkyl residues.

In a further preferred embodiment $R^2$ and $R^3$ together form a ring having 5 to 8 and especially preferred 5 or 6 ring atoms, including the nitrogen atom carrying the residues $R^2$ and $R^3$. Preferably the further ring atoms are carbon atoms. In a further preferred embodiment the ring comprises, besides carbon atoms, one or two ring atoms selected from N, O and S. Examples for preferred cyclic structures are 1-piperidyl, pyrrolidin-1-yl, piperazin-1-yl and morpholinyl residues. The ring formed by $R^2$ and $R^3$ may be substituted with one, two or three substituents. In a preferred embodiment the ring carries one substituent. Preferred substituents are alkyl residues having 1 to 4 carbon atoms as for example methyl, ethyl, n-propyl, isopropyl, n-butyl, isobutyl and tert.-butyl groups. The substituent may be bound to a carbon atom. Preferably it is bound to a nitrogen atom, if present.

Preferably B is an alkylene group having 2, 3 or 4 carbon atoms. Especially preferred B is an ethylene or a propylene group. When B has 3 or more carbon atoms it may be straight-chain or branched. In a more preferred embodiment B is an ethylene group having the formula —$CH_2$—$CH_2$— and in an especially preferred embodiment B is a propylene group having the formula —$CH_2$—$CH_2$—$CH_2$—.

Y is a group of formula $NR^5$, wherein $R^5$ preferably is hydrogen or an alkyl group having 1 to 4 carbon atoms as for example a methyl, ethyl, propyl, isopropyl, butyl, isobutyl or ter.-butyl group. Especially preferred $R^5$ is hydrogen.

In a preferred embodiment B and Y are constituents of a N,N-dialkylaminoalkylene amine according to formula (IVa) being one of the raw materials used for the synthesis of the N-alkyl-N'—(N",N"-dialkylaminoalkyl)dicarboxylic acid diamide (I),

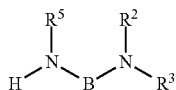

wherein
B, $R^2$, $R^3$ and $R^5$ have the meanings given above.

Examples for preferred N,N-dialkylaminoalkyleneamines according to formula (IV) are N,N-dimethylaminoethylamine, N,N-dimethylaminopropylamine, N,N-dimethylaminobutylamine, N,N-diethylaminoethylamine, N,N-diethylaminopropylamine, N,N-dipropylaminoethylamine, N,N-dipropylaminopropylamine, N,N-dibutylaminoethylamine, N,N-dibutylaminopropylamine, N,N-dimethylamino-2-hydroxypropylamine, N-(3-aminopropyl)pyrrolidine, N-(3-aminopropyl)piperidine, 1-(3-aminopropyl)-piperazine and 1-(3-aminopropyl)-4-methylpiperazine. The preparation of N,N-dialkylaminoalkylenamines is described for example in *Journal of the American Chemical Society* 1944 66(5), 725-731.

Acid

Preferably $M^-$ is an anion selected from sulfate, sulfide, carbonate, bicarbonate, nitrate, the halogenides and the carboxylates. Examples for suited halogenides are fluoride, chloride and iodide. Especially preferred anions are carboxylates derived from carboxylic acids. Preferred carboxylic acids have the formula (V),

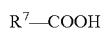

wherein $R^7$ is hydrogen or an optionally substituted hydrocarbyl residue having between 1 and 22 carbon atoms, preferably between 2 and 12 carbon atoms and especially preferred between 3 and 6 carbon atoms as for example between 1 and 12 carbon atoms, or between 1 and 6 carbon atoms, or between 2 and 22 carbon atoms, or between 2 and 6 carbon atoms, or between 3 and 22 carbon atoms, or between 3 and 12 carbon atoms.

In preferred carboxylic acids according to formula (V) the optionally substituted hydrocarbyl residue $R^7$ is an alkyl or alkenyl residue. The alkyl or alkenyl residue may be linear or, when having three or more carbon atoms, may be branched. Preferred alkenyl residues $R^7$ have one or more as for example one, two or three double bonds. Preferred substituents are hydroxy groups, carboxylic acid groups and amino groups. In a preferred embodiment the hydrocarbyl residue $R^7$ does not comprise heteroatoms. Preferred carboxylic acids include natural and synthetic fatty acids. Carboxylic acids based on renewable raw materials are especially preferred. Such fatty acids are obtainable for example by saponification of naturally occurring oils and fats and optionally further derivatization.

Examples for preferred carboxylic acids $R^7$—COOH (V) are formic acid, acetic acid, propionic acid, butyric acid, pivalic acid, hexanoic acid, octanoic acid, 2-ethyl hexanoic acid, decanoic acid neodecanoic acid, dodecanoic acid, neodecanoic acid, neoundecanoic acid, dodecanoic acid, tetradecanoic acid, hexadecanoic acid, octadecanoic acid, acrylic acid, methacrylic acid and their mixtures. Mixtures of carboxylic acids may contain acids with different chain lengths, with different degrees of unsaturation and/or different degrees of branching. Especially preferred are mixtures of fatty acids based on natural fats and oils as for example coco fatty acid, rape seed fatty acid, soya fatty acid, palm fatty acid, palm kernel fatty acid, tallow fatty acid, and tall oil fatty acid. These fatty acid mixtures may be used as such or upon hydrogenation respectively partial hydrogenation. In an especially preferred embodiment $R^7$ is a saturated $C_1$- to $C_4$ alkyl residue. In a further especially preferred embodiment $R^7$ is an unsaturated $C_3$- to $C_6$ alkenyl residue. Examples for especially preferred carboxylic acids are acrylic acid, methacrylic acid, acetic acid, propanoic acid, butanoic acid, octanoic acid, dodecanoic acid, tetradecanoic acid and coconut fatty acid.

Examples for chemical structures of particularly preferred N-alkyl-N'—(N'',N''-dialkylammoniumalkyl)dicarboxylic acid diamide salts according to formula (I) are given in the following formulae (Ib) to (If):

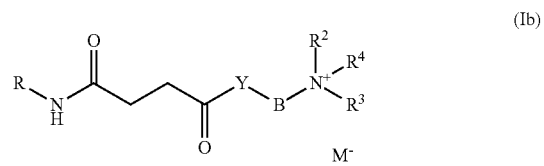

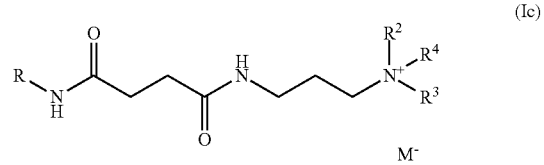

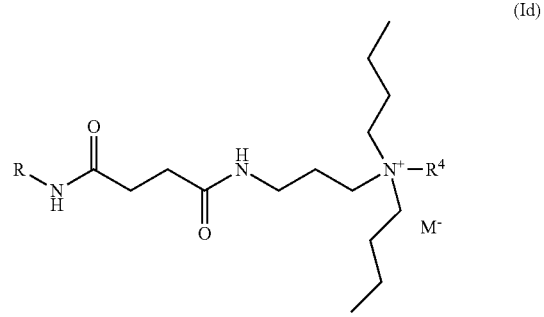

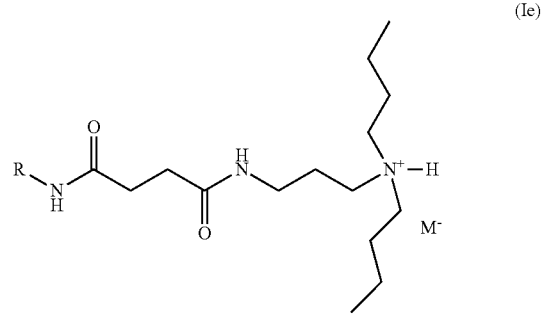

wherein
R, Y, B, $R^2$, $R^3R^4$ and $M^-$ have the meanings given above.

In a preferred embodiment most of the starting dicarboxylic acid, the fatty amine and/or the carboxylic acid are selected from renewable materials. In an especially preferred embodiment all or at least essentially all of the starting dicarboxylic acid, the fatty amine and/or the carboxylic acid are selected from renewable materials. Accordingly the hydrate inhibitors according to the invention are considered to be renewable.

Starting from dicarboxylic acids, N,N-dialkylaminoalkyleneamines and fatty amines enables to produce N-alkyl-N'—(N'',N''-dialkylaminoalkyl)dicarboxylic acid diamides and their salts according to the invention in only three reaction steps. In a preferred embodiment the production of the hydrate inhibitors (I) proceeds without the formation of by-products (except water).

The compounds according to the invention may be prepared by reacting a N,N-disubstituted alkylenediamine with a dicarboxylic acid (or its reactive derivative) to give the corresponding mono- and/or dicarboxamides and/or cyclic dicarboximides, in accordance with the molar ratio of the reactants. In a preferred embodiment the N,N-disubstituted alkylenediamine and the dicarboxylic acid (respectively its reactive derivative) are reacted in essentially equimolar amounts to give predominantly a cyclic dicarboximide. Essentially equimolar amounts includes molar ratios of the reactants between 1.5:1 and 1:1.5, preferably between 1.2:1 and 1:1.2 and especially between 1:1.05 and 1.05:1. Subsequently the monocarboxamides and/or cyclic dicarboximides are reacted with a fatty amine to give the N-alkyl-N'—(N",N"-dialkylaminoalkyl)dicarboxylic acid diamide (11).

In this reaction sequence the dicarboxylic acid or its reactive derivative is generally reacted with the N,N-disubstituted alkylenediamine at a temperature of between 100 and 240° C., preferably at a temperature of between 120 and 200° C., as for example between 100 and 200° C. or between 120 and 240° C. In a preferred embodiment the condensation to the corresponding mono- or dicarboxamides, in some cases to cyclic dicarboximides, with elimination of water of reaction or of alcohol is complete. The degree of reaction can be followed by determination of the acid number, hydrolysis number and/or by the determination of the base and/or amide nitrogen. Subsequently the ring opening reaction of the cyclic imide intermediate with a fatty amine may be made by heating the reaction mixture to a temperature of between 50° C. and 150° C., for a duration of 1 min to 20 hours, as for example for 0.5 to 5 hours, to form the N-aminoalkyl-N'—(N",N"-dialkylamino)dicarboxylic acid diamide of formula (II) In a preferred embodiment the N-alkyl-N'—(N",N"-dialkylaminoalkyl)dicarboxylic acid diamides according to formula (II) are prepared by stepwise chemical reactions as shown below:

In a first step the dicarboxylic acid is condensed with the fatty amine to form a cyclic imide intermediate as represented by formula (VI),

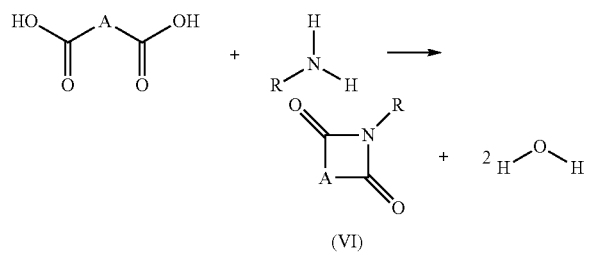

wherein
A and R have the meanings given above.

In a preferred embodiment the fatty amine and the dicarboxylic acid (or its reactive derivative) are reacted in essentially equimolar amounts to give predominantly a cyclic dicarboximide of formula (VI). Essentially equimolar amounts includes molar ratios of the reactants between 1.5:1 and 1:1.5, preferably between 1.2:1 and 1:1.2 and especially between 1:1.05 and 1.05:1. Preferably the reaction is made at temperatures between 100 and 240° C. and especially between 120 and 200° C. as for example between 100 and 200° C. or between 120 and 240° C. The imidation reaction is suitably effected by heating the mixture for a period of from 2 to 20 hours. The pressure is preferably between 0.001 and 1.2 bar and more preferred between 0.01 and 1.0 bar. Often a reduced pressure of from 5 to 200 mbar has proven to be advantageous.

In a subsequent second reaction step the intermediate cyclic imide intermediate (VI) is reacted with a N,N-disubstituted alkylenediamine of formula (IV) to form the N-alkyl-N'—(N",N"-dialkylaminoalkyl)dicarboxylic acid diamide according to formula (II).

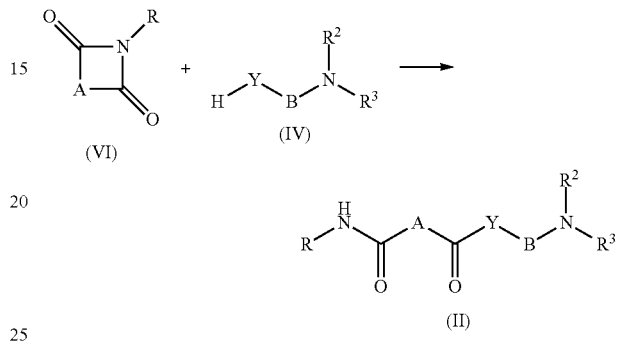

wherein
A, B, Y, R, $R^2$ and $R^3$ have the meanings given above.

The ring opening reaction of the cyclic imide intermediate (VI) with an N,N-disubstituted alkylenediamine may be made by heating the reaction mixture to a temperature of between 50° C. and 150° C., for a duration of 1 min to 20 hours as for example for 0.5 to 5 hours, to form the N-alkyl-N'—(N",N"-dialkylaminoalkyl)dicarboxylic acid diamide of formula (II).

In the second reaction step of both reaction pathways preference is given to using an excess of the amine (fatty amine respectively N,N-dialkylaminoalkyleneamine) with respect to the cyclic imide intermediate (VI) and subsequent removal of the excess amine by distillation.

When starting from dicarboxylic acid esters as the reactive derivative of the dicarboxylic acid (III) the alcohol released during the reaction is preferably removed by distillation. When starting from dicarboxylic anhydrides the reaction may include intermediate esterification with a lower alcohol, followed by aminolysis of the ester. Suitable alcohols are, for example, ethanol, propanol, isopropanol or 2-ethylhexanol. Particular preference is given to 2-ethylhexanol.

When preparing the unsymmetric diamides (II), some of the intermediate cyclic dicarboximides (VI) as well as respective dicarboxydiamides may remain in the product and form part of the gas hydrate inhibitor formulation.

The amidation reactions of the first and second step can be accelerated by addition of acidic catalysts having a pKa of less than or equal to 5. Bronstedt and Lewis acids are preferred. Examples for suited catalysts are mineral acids like sulfuric acid, methanesulfonic acid, p-toluenesulfonic acid, dodecylbenzenesulfonic acid, hypophosphorous acid, phosphorous acid, citric acid and $BF_3$. Particular preference is given to alkylstannic acids. Typically 0.001 to 0.5 wt.-% and preferably 0.005 to 0.15 wt.-% of the catalyst in respect to the mass of the dicarboxylic acid and the amine are used.

In a third step the N-alkyl-N'—(N",N"-dialkylaminoalkyl)dicarboxylic acid diamide (II) is reacted with an acid to form the N-alkyl-N'—(N",N"-dialkylammoniumalkyl)dicarboxylic acid diamide salt according to formula (I).

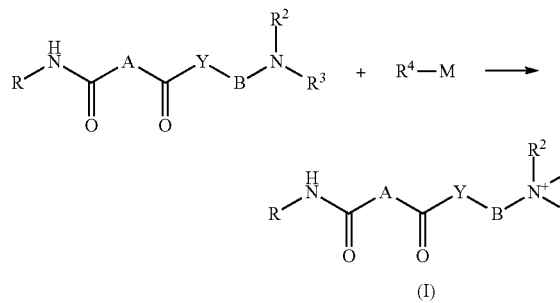

wherein
A, B, Y, R, $R^2$, $R^3$, $R^4$ and $M^-$ have the meanings given above.

Preferably the salt formation of the N-alkyl-N'—(N'',N''-dialkylaminoalkyl)dicarboxylic acid diamide (II) with an acid of formula (V) is made by mixing the N-alkyl-N'—(N'',N''-dialkylaminoalkyl)dicarboxylic acid diamide (II) with the acid to give the corresponding N-alkyl-N'—(N'',N''-dialkylammoniumalkyl)dicarboxylic acid diamide salt (I).

Preferably the formation of the salt is made at temperatures between ambient and 100° C. and more preferably at temperatures between 30 and 60° C. as for example between 30 and 100° C. or between ambient and 60° C. Preferably the acid is added to the N-alkyl-N'—(N'',N''-dialkylaminoalkyl)dicarboxylic acid diamide (II) in a manner that the temperature does not exceed 100° C. and more preferably not 70° C. Preferably the acid and the N-alkyl-N'—(N'',N''-dialkylaminoalkyl)dicarboxylic acid diamide (II) are reacted in a molar ratio of between 1:10 and 2:1, more preferably between 1:8 and 1.5:1 and especially preferred between 1:2 and 1:1, as for example between 1:10 and 1.5:1, or between 1:10 and 1:1, or between 1:8 and 2:1, or between 1:8 and 1:1, or between 1:2 and 2:1, or between 1:2 and 1.5:1. In a specific embodiment acid and N-alkyl-N'—(N'',N''-dialkylaminoalkyl)dicarboxylic acid diamide (II) are reacted in equimolar quantities. The given molar ratios refer to the number of carboxylic acid groups in respect to amine groups.

The thus produced N-alkyl-N'—(N'',N''-dialkylammoniumalkyl)dicarboxylic acid diamide salt (I) may be purified by any methods known to the skilled in the art, e.g. by filtration, distillation or recrystallization. However, in most cases the crude reaction product has proven to be suited for direct application.

The reaction sequence can be executed solvent free. However, in many cases it has proven to be advantageous to conduct the reaction or at least one or more of the reaction steps in the presence of a solvent. Especially for the reaction of dicarboxylic acids the presence of a solvent is preferred when a high conversion and/or a low acid number of the resulting reaction product is targeted.

Preferred solvents for the reaction are organic solvents which allow for azeotropic removal of the water of reaction. In particular, aromatic solvents or solvent mixtures, or alcohols, can be used. Particular preference is given to solvents having a boiling point of at least 100° C. and preferably 110 to 200° C. under standard conditions. Examples of suitable solvents are decane, toluene, xylene, diethylbenzene, naphthalene, tetralin, decalin, and commercial solvent mixtures such as Shellsol®, Exxsol®, Isopar®, Solvesso® types, Solvent Naphtha and/or kerosene. In a preferred embodiment, the solvent comprises at least 10% by weight, preferably 20 to 100% by weight, for example 30 to 90% by weight, of aromatic constituents. Shellsol® and Exxsol® grades are obtainable form Shell and ExxonMobil, respectively. The reaction is then effected at the boiling point of the azeotrope.

In a preferred embodiment the N-alkyl-N'—(N'',N''-dialkylammoniumalkyl)dicarboxylic acid diamide salt (I) is used in combination with a N-alkyl-N'—(N'',N''-dialkylaminoalkyl)dicarboxylic acid diamide (II). Preferably the portions of both species (I) and (II) in such mixtures are between 100:1 and 1:100, more preferably between 20:1 and 1:20, more preferably between 10:1 and 1:10 and especially preferred between 5:1 and 1:2 as for example between 100:1 and 1:20, or between 100:1 and 1:10, or between 100:1 and 1:2, or between 201 and 1:100, or between 20:1 and 1:10, or between 20:1 and 1:2, or between 10:1 and 1:100, or between 10:1 and 1:20, or between 10:1 and 1:2, or between 5:1 and 1:100, or between 5:1 and 1:20, or between 5:1 and 1:10.

For the inhibition of gas hydrates N-alkyl-N'—(N'',N''-dialkylammoniumalkyl)dicarboxylic acid diamides salts according to formula (I) are the most effective component. These salts provide improved performance as anti-agglomeration agent for gas hydrates over the additives according to the state of the art. However, the salts can equally be generated in situ by injecting the N-alkyl-N'—(N'',N''-dialkylaminoalkyl)dicarboxylic acid diamide according to formula (II) and the carboxylic acid (V) separately in to the fluid to be treated. In an alternative embodiment, in acidic fluids the acid present may serve to convert the N-alkyl-N'—(N'',N''-dialkylaminoalkyl)dicarboxylic acid diamide (II) into its salt (I). This is applicable for fluids having a pH below 8 and especially having a pH of 7 or less.

For the use as a gas hydrate inhibitor according to the third aspect of the invention the gas hydrate inhibitor according to the first aspect of the invention is added to the system to be inhibited from gas hydrate agglomeration. Preferably, the hydrate inhibitor is injected into the system to be inhibited at a point and under conditions (p, T) where no or only little formation of hydrates has occurred. An exemplary injection point for petroleum production operations is downhole near the surface controlled sub-sea safety valve. This ensures that during a shut-in, the product is able to disperse throughout the area where hydrates will occur. Treatment can also occur at other areas in the flowline, taking into account the density of the injected fluid. If the injection point is well above the hydrate formation depth, then the hydrate inhibitor can be formulated with a solvent having a density high enough that the inhibitor will sink in the flowline to collect at the water/oil interface. Moreover, the treatment can also be used in pipelines or anywhere in the system where the potential for hydrate formation exists.

In a preferred embodiment the system to be inhibited from gas hydrate formation is a petroleum fluid being the mixture of varying amounts of water/brine, crude oil/condensate, and natural gas. The petroleum fluid may contain various levels of salinity. The fluid can have a salinity of about 0% to about 25% or about 10% to about 25% weight/weight (w/w) total dissolved solids (TDS). The petroleum fluids in which the gas hydrate inhibitor according to the first and second aspect of the invention is applied can be contained in many different types of apparatuses, especially those that transport an aqueous medium from one location to another. In a preferred embodiment the petroleum fluid is contained in an oil and gas pipeline. In a further preferred embodiment the petroleum fluid to be treated can be contained in refineries, such as separation vessels, dehydration units, gas lines, and pipelines.

The gas hydrate inhibitors according to the first and second aspect of the invention are generally used in amounts of between 0.01 and 5% by volume (based on the volume of the aqueous phase), corresponding to 100-50 000 vol.-ppm, preferably from 0.02 to 1% by volume. These amounts apply to the method of the fourth aspect as well.

The gas hydrate inhibitors according to the invention may be used as such or in a formulation containing a solvent and/or other actives. This applies to the method of the fourth aspect as well.

For their use as gas hydrate inhibitors according to the third aspect of the invention and for the method for inhibiting the agglomeration of gas hydrates according to the fourth aspect of the invention, the gas hydrate inhibitors according to the first aspect of the invention are preferably used as a formulation in an organic solvent. This facilitates the handling of the inhibitors and furthermore it often supports dispersion of the hydrate crystals. In a first embodiment alcoholic solvents such as water-soluble mono-, di- and polyhydric alcohols. Examples for suited alcohols are methanol, ethanol, propanol, butanol, ethylene glycol, propylene glycol, butyl glycol, glycerin and also oxyethylated monoalcohols such as 2-butoxyethanol, isobutyl glycol, butyl diglycol and polyglycols such as diethylene glycol are particularly preferred. Especially preferred alcohol is 2-butoxyethanol. In a further embodiment higher boiling aliphatic, aromatic and alkylaromatic hydrocarbons and mixtures thereof have proven to be advantageous. In particular, aromatic solvents or solvent mixtures are used. Examples of suitable solvents are decane, toluene, xylene, diethylbenzene, naphthalene, tetralin, decalin, and commercial solvent mixtures such as Shellsol®, Exxsol®, Isopar®, Solvesso® types, diesel, Solvent Naphtha and/or kerosene. In a preferred embodiment, the solvent comprises at least 10% by weight, preferably 20 to 100% by weight, for example 30 to 90% by weight, of aromatic constituents. Shellsol® and Exxsol® grades are obtainable form Shell and ExxonMobil, respectively. A further preferred solvent is water.

In some cases, the gas hydrate inhibitor can include a majority of solvent, and in some cases the gas hydrate inhibitor can include up to 50% by weight of a solvent. A solvent could be present with the gas hydrate inhibitor on a weight basis of about 0.01 to about 50%, or 0.1 to about 40% or 0.5 to about 30%, or even from about 1.0 to about 25%. In some embodiments a solvent can be present at about 1.5 to about 20%, or 2.0 to about 15% or even 2.5 or 5 to about 10%.

An example of a gas hydrate inhibitor additive may contain 10 to 30 percent by weight of the described N-alkyl-N'—(N",N"-dialkylammoniumalkyl)dicarboxylic acid diamide salt (I) and 70 to 90 percent by weight of an alcohol such as methanol. Another example of a gas hydrate inhibitor anti-agglomerate additive may contain 10 to 30 percent by weight of the N-alkyl-N'—(N",N"-dialkylammoniumalkyl)dicarboxylic acid diamide salt (I) and 10 to 30 percent by weight of a polymeric kinetic inhibitor, 20 to 40 percent by weight water, and 20 to 40 percent by weight of ethylene glycol.

Particularly suitable gas hydrate inhibitors and therefore a preferred embodiment of this invention are mixtures of two or more compounds of general formula (II) and/or (I) differing in at least one feature, e.g. in the alkyl chain length of R.

In a further preferred embodiment the compounds of the formula (II) and/or (I) are used together with one or more polymers known to inhibit the formation of hydrates in order to further improve the performance of the additives according to the invention, as for example to reduce the overall dosage rate. Preferred further hydrate inhibitors are polymers having a carbon backbone and amide bonds in the side chains. These include in particular homo- and copolymers based on vinylpyrrolidone, vinylcaprolactam, isopropylacrylamide, acryloylpyrrolidine, N-acryloylmorpholine, N-acryloylpiperidine and/or N-methyl-N-vinylacetamide, and optionally containing further anionic, cationic and neutral comonomers having a vinylic double bond, such as for example 2-dimethylaminoethyl methacrylate, 1-olefins, N-alkylacrylamides, N-vinylacetamide, acrylamide, sodium 2-acrylamido-2-methyl-1-propanesulfonate (AMPS) or acrylic acid.

Likewise suitable are mixtures with alkylpolyglycosides, hydroxyethylcellulose, carboxymethylcellulose and also other ionic or nonionic surfactant molecules.

When mixtures of different gas hydrate inhibitors are used, the concentration ratios between the gas hydrate inhibitors according to the invention and the mixed-in components is preferably between 90:10 and 10:90 percent by weight, more preferably between 75:25 and 25:75, and especially between 60:40 and 40:60 as for example between 90:10 and 25:75, or between 90:10 and 40:60, or between 75:25 and 10:90, or between 75:25 and 40:60, or between 60:40 and 10:90, or between 60:40 and 25:75.

Usually such mixtures allow for further reduction of the treat rate of the gas hydrate inhibitor according to the invention and preferably they allow for a reduction of the overall dosage rate. When the gas hydrate inhibitors according to the invention are used in a mixture with other gas hydrate inhibitors, the concentration of the mixture is from 0.01 to 2% by weight or from 0.02 to 1% by weight, in the aqueous phase to be treated.

The gas hydrate inhibitors according to the invention, like their mixtures with other gas hydrate inhibitors, can be added to a multiphase mixture which is prone to hydrate formation in the course of crude oil and natural gas extraction or in the course of provision of drilling muds using common equipment such as injection pumps or the like; as a consequence of the good solubility of the inhibitors according to the invention, there is rapid and uniform distribution of the inhibitor in the aqueous phase or the condensate phase tending to hydrate formation.

All percent values are given in percent by weight unless otherwise specified.

EXAMPLES

General Method for the Preparation of N-alkyl-N'—(N",N"-dialkylaminoalkyl)dicarboxylic acid diamides Starting from Dicarboxylic Acids The amounts of dicarboxylic acid, fatty amine and optionally solvent given in the reaction protocols below were charged into a five-neck flask equipped with distillation condenser or optionally a Dean-Stark trap connected with a reflux condenser, overhead stirrer, internal thermometer and nitrogen inlet tube. The temperature of the mixture was increased to 130° C. while gently stirring. As the temperature approached 130° C., the mixture slowly melted to a tan liquid. Heating and stirring were continued with continuous removal of water from the reaction mixture.

The progress of the reaction was monitored by potentiometric amine number titration of aliquots of the reaction mixture with perchloric acid. Amine number is abbreviated as AN. It was determined by potentiometric titration of the sample with perchloric acid after dilution of the sample with acetic acid. When titration showed AN≤1 mmol/g, the formation of the cyclic imide intermediate was considered to be completed. The cyclic imide product was characterized by $^1$H-NMR spectroscopy (CDCl$_3$, δ=2.67 ppm, 4H singlet).

The reaction mixture was cooled down to 80° C. and an equimolar amount of the diamino alkane given in the respective protocol was added to the reaction mixture.

The reaction mixture was heated to 120-130° C. with stirring for up to 18 hours. The reaction progress was followed by means of $^1$H-NMR spectroscopy. When the four symmetric ring hydrogen signals of the cyclic imide structure at δ=2.67 ppm in the $^1$H-NMR spectrum were no longer visible the reaction was stopped. The unsymmetric diamide structure was confirmed by $^1$H-NMR.

Example 1: N-dodecyl-N'-[3-(dimethylamino)propyl]-succinic acid diamide 100 g (0.85 mol) of succinic acid, 156.96 g (0.85 mol) of dodecylamine and 86.85 g (0.85 mol) of N,N-dimethyl-propane-1,3-diamine were used to obtain 298 g of N-dodecyl-N'-[3-(dimethylamino)propyl]-succinic acid diamide as a brownish solid.

Example 2: N-dodecyl-N'-[6-(dimethylamino)hexyl]-succinic acid diamide 100 g (0.85 mol) of succinic acid, 156.96 g (0.85 mol) of dodecylamine and 122.62 g (0.85 mol) of N,N-dimethyl-hexane-1,6-diamine were used to obtain 330 g of N-dodecyl-N'-[6-(dimethylamino)hexyl]-succinic acid diamide as a brownish solid.

Example 3: N-dodecyl-N'-[3-(dibutylamino)propyl]-succinic acid diamide 100 g (0.85 mol) of succinic acid, 156.96 g (0.85 mol) of dodecylamine and 158.40 g (0.85 mol) of N,N-dibutyl-propane-1,3-diamine were used to obtain 379 g of N-dodecyl-N'-[3-(dibutylamino)propyl]-succinic acid diamide as a brownish solid.

Example 4: N-cocoyl-N'-[3-(dibutylamino)propyl]-succinic acid diamide 100 g (0.85 mol) of succinic acid, 166.14 g (0.85 mol) of cocoylamine (AN=287.15 mgKOH/g) and 158.40 g (0.85 mol) of N,N-dibutyl-propane-1,3-diamine were used to obtain 374 g of N-cocoyl-N'-[3-(dibutylamino)propyl]-succinic acid diamide as a brownish solid.

Example 5: N-dodecyl-N'-[3-(dibutylamino)propyl]-malic acid diamide 114 g (0.85 mol) of malic acid, 156.96 g (0.85 mol) of dodecylamine and 158.40 g (0.85 mol) of N,N-dibutyl-propane-1,3-diamine were used to obtain 392 g of N-dodecyl-N'-[3-(dibutylamino)propyl]-malic acid diamide as a brownish solid.

Example 6: N-cocoyl-N'-[3-(dibutylamino)propyl]-malic acid diamide 114 g (0.85 mol) of malic acid, 166.14 g (0.85 mol) of cocoylamine (AN=287.15 mgKOH/g) and 158.40 g (0.85 mol) of N,N-dibutyl-propane-1,3-diamine were used to obtain 397 g of N-cocoyl-N'-[3-(dibutylamino)propyl]-malic acid diamide as a brownish solid.

Example 7: N-dodecyl-N'-[3-(dibutylamino)propyl]-tartaric acid diamide 127.58 g (0.85 mol) of tartaric acid, 156.96 g (0.85 mol) of dodecylamine and 158.40 g (0.85 mol) of N,N-dibutyl-propane-1,3-diamine were used to obtain 408 g of N-dodecyl-N'-[3-(dibutylamino)propyl]-tartaric acid diamide as a brownish solid.

Example 8: N-cocoyl-N'-[3-(dibutylamino)propyl]-tartaric acid diamide 127.58 g (0.85 mol) of tartaric acid, 166.14 g (0.85 mol) of cocoylamine (AN=287.15 mgKOH/g) and 158.40 g (0.85 mol) of N,N-dibutyl-propane-1,3-diamine were used to obtain 400 g of N-cocoyl-N'-[3-(dibutylamino)propyl]-tartaric acid diamide as a brownish solid.

Example 9: N-dodecyl-N'-[4-(dibutylamino)butyl]-succinic acid diamide 100 g (0.85 mol) of succinic acid, 156.96 g (0.85 mol) of dodecylamine and 170.31 g (0.85 mol) of N,N-dibutyl-butane-1,4-diamine were used to obtain 401 g of N-dodecyl-N'-[4-(dibutylamino)butyl]-succinic acid diamide as a brownish solid.

Example 10: N-dodecyl-N'-[2-(dibutylamino)ethyl]-succinic acid diamide 100 g (0.85 mol) of succinic acid, 156.96 g (0.85 mol) of dodecylamine and 146.48 g (0.85 mol) of N,N-dibutyl-ethane-1,2-diamine were used to obtain 363 g of N-dodecyl-N'-[2-(dibutylamino)ethyl]-succinic acid diamide as a brownish solid.

Example 11: N-dodecyl-N'-[3-(dibutylamino)propyl]-phthalic acid diamide 141.21 g (0.85 mol) of phthalic acid, 156.96 g (0.85 mol) of dodecylamine and 158.40 g (0.85 mol) of N,N-dibutyl-propane-1,3-diamine were used to obtain 407 g of N-dodecyl-N'-[3-(dibutylamino)propyl]-phthalic acid diamide as a brownish solid.

Example 12: N-dodecyl-N'-[3-(1-piperidyl)propyl]-succinic acid diamide 100 g (0.85 mol) of succinic acid, 156.96 g (0.85 mol) of dodecylamine and 167.34 g (0.85 mol) of 3-piperidinopropylamine were used to obtain 301 g of N-dodecyl-N'-[3-(1-piperidyl)propyl]-succinic acid diamide as a brownish solid.

Example 13: N-dodecyl-N'-[3-(4-methylpiperazin-1-yl]-succinic acid diamide 100 g (0.85 mol) of succinic acid, 156.96 g (0.85 mol) of dodecylamine and 185.00 g (0.85 mol) of 3-(4-methylpiperazin-1-yl)propylamine were used to obtain 301 g of N-dodecyl-N'-[3-(4-methylpiperazin-1-yl]-succinic acid diamide as a brownish solid.

Example 14: N-dodecyl-N-methyl-N'-[3-(dibutylamino)propyl]-succinic acid diamide 100 g (0.85 mol) of succinic acid, 169.47 g (0.85 mol) of N-methyldodecylamine and 158.40 g (0.85 mol) of N,N- dibutyl-propane-1,3-diamine were used to obtain 390 g of N-dodecyl-N-methyl-N'-[3-(dibutylamino)propyl]-succinic acid diamide as a brownish solid.

Example 15: N-dodecyl-N'-[3-(dibutylamino)propyl]-malonic acid diamide 100 g (0.96 mol) of malonic acid, 177.94 g (0.96 mol) of dodecylamine and 178.88 g (0.96 mol) of N,N-dibutyl-propane-1,3-diamine were used to obtain 450 g of N-dodecyl-N'-[3-(dibutylamino)propyl]-malonic acid diamide as a brownish solid.

Example 16: N-[3-(Dibutylamino)-propyl]-N'-dodecyl-succinamide; Preparation in Xylene 100 g (0.85 mol) of succinic acid, 156.96 g (0.85 mol) of dodecylamine, xylene 415 g and 158.40 g (0.85 mol) of N,N-dibutyl-propane-1,3-diamine were used to obtain 379 g of a 50% active solution of N-[3-(dibutylamino)-propyl]-N'-dodecyl-succinamide in xylene.

General Method for the Preparation of N-alkyl-N'—(N",N"-dialkylammoniumalkyl)dicarboxylic acid diamide salts A reaction flask equipped with overhead stirrer, reflux condenser and thermometer was charged with equimolar amounts of an N-alkyl-N'—(N",N"-dialkylaminoalkyl)dicarboxylic acid diamide synthesized in examples 1 to 16, the solvent and the acid given in examples 17 to 35. The temperature of the apparatus was increased to 50° C. and the mixture was gently stirred for 2 hours.

Example 17: N-dodecyl-N'-[3-(dibutylammonium)propyl]-succinic acid diamide acrylate 100 g (0.22 mol) of N-dodecyl-N'-[3-(dibutylamino)propyl]-succinic acid diamide according to example 3, 15.66 g (0.22 mol) acrylic acid and 115.66 g methanol were used to obtain 231.32 g of a 50% active solution of N-dodecyl-N'-[3-(dibutylammonium)propyl]-succinic acid diamide acrylate in methanol.

Example 18: N-dodecyl-N'-[3-(dibutylammonium)propyl]-succinic acid diamide acetate 100 g (0.22 mol) of N-dodecyl-N'-[3-(dibutylamino)propyl]-succinic acid diamide according to example 3, 12.99 g (0.22 mol) acetic acid and 112.99 g methanol were used to obtain 126 g of a 50% active solution of N-dodecyl-N'-[3-(dibutylammonium)propyl]-succinic acid diamide acetate in methanol.

Example 19: N-dodecyl-N'-[3-(dibutylammonium)propyl]-succinic acid diamide dodecanoate 100 g (0.22 mol) of N-dodecyl-N'-[3-(dibutylamino)propyl]-succinic acid diamide according to example 3, 44.07 g (0.22 mol) dodecanoic acid and 144.07 g methanol were used to obtain 288, 14 g of a 50% active solution of N-dodecyl-N'-[3-(dibutylammonium)propyl]-succinic acid diamide dodecanoate in methanol.

Example 20: N-dodecyl-N'-[3-(dibutylammonium)propyl]-succinic acid diamide cocoate 100 g (0.22 mol) of N-dodecyl-N'-[3-(dibutylamino)propyl]-succinic acid diamide according to example 3, 48.04 g (0.22 mol) coconut fatty acid and 148.04 g methanol were used to obtain 296.08 g of a 50% active solution of N-dodecyl-N'-[3-(dibutylammonium)propyl]-succinic acid diamide cocoate in methanol.

Example 21: N-cocoyl-N'-[3-(dibutylammonium)propyl]-succinic acid diamide acrylate 100 g (0.21 mol) of N-cocoyl-N'-[3-(dibutylamino)propyl]-succinic acid diamide according to example 4, 15.13 g (0.21 mol) acrylic acid and 115.13 g methanol were used to obtain 130.26 g of a 50% active solution of N-cocoyl-N'-[3-(dibutylammonium)propyl]-succinic acid diamide acrylate in methanol.

Example 22: N-dodecyl-N'-[3-(dibutylammonium)propyl]-succinic acid diamide acrylate 100 g (0.11 mol) of 50% active solution of N-dodecyl-N'-[3-(dibutylamino)propyl]-succinic acid diamide in xylene according to example 15 and 7.83 g (0.11 mol) acrylic acid were used to obtain 107.83 g of a 50% active solution of N-dodecyl-N'-[3-(dibutylammonium)propyl]-succinic acid diamide acrylate in xylene.

Example 23: N-dodecyl-N'-[3-(dibutylammonium)propyl]-malic acid diamide acrylate 100 g (0.21 mol) of N-dodecyl-N'-[3-(dibutylamino)propyl]-malic acid diamide according to example 5, 15.34 g (0.21 mol) acrylic acid and 115.34 g methanol were used to obtain 230.68 g of a 50% active solution of N-dodecyl-N'-[3-(dibutylammonium)propyl]-malic acid diamide acrylate in methanol.

Example 24: N-cocoyl-N'-[3-(dibutylammonium)propyl]-malic acid diamide acrylate 100 g (0.22 mol) of N-cocoyl-N'-[3-(dibutylamino)propyl]-malic acid diamide according to example 6, 15.85 g (0.22 mol) acrylic acid and 115.85 g methanol were used to obtain 231.7 g of a 50% active solution of N-cocoyl-N'-[3-(dibutylammonium)propyl]-malic acid diamide acrylate in methanol.

Example 25: N-dodecyl-N'-[3-(dibutylammonium)propyl]-tartaric acid diamide acrylate 100 g (0.21 mol) of N-dodecyl-N'-[3-(dibutylamino)propyl]-tartaric acid diamide according to example 7, 15.34 g (0.21 mol) acrylic acid and 115.34 g methanol were used to obtain 230.68 g of a 50% active solution of N-dodecyl-N'-[3-(dibutylammonium)propyl]-tartaric acid diamide acrylate in methanol.

Example 26: N-cocoyl-N'-[3-(dibutylammonium)propyl]-tartaric acid diamide acrylate 100 g (0.23 mol) of N-cocoyl-N'-[3-(dibutylamino)propyl]-tartaric acid diamide according to example 8, 16.57 g (0.23 mol) acrylic acid and 116.57 g methanol were used to obtain 233.14 g of a 50% active solution N-cocoyl-N'-[3-(dibutylammonium)propyl]-tartaric acid diamide acrylate in methanol.

Example 27: N-dodecyl-N'-[4-(dibutylammonium)butyl]-succinic acid diamide acrylate 100 g (0.26 mol) of N-dodecyl-N'-[4-(dibutylamino)butyl]-succinic acid diamide according to example 9, 18.72 g (0.26 mol) acrylic acid and 118.72 g methanol were used to obtain 237.44 g of a 50% active solution of N-dodecyl-N'-[4-(dibutylammonium)butyl]-succinic acid diamide acrylate in methanol.

Example 28: N-dodecyl-N'-[2-(dibutylammonium)ethyl]-succinic acid diamide acrylate 100 g (0.23 mol) of N-dodecyl-N'-[2-(dibutylamino)ethyl]-succinic acid diamide according to example 10, 16.38 g (0.23 mol) acrylic acid and 116.38 g methanol were used to obtain 232.77 g of a 50% active solution of N-dodecyl-N'-[2-(dibutylammonium)ethyl]-succinic acid diamide acrylate in methanol.

Example 29: N-dodecyl-N'-[3-(dimethylammonium)propyl]-succinic acid diamide acrylate 100 g (0.27 mol) of N-dodecyl-N'-[3-(dimethylamino)propyl]-succinic acid diamide according to example 1, 19.48 g (0.23 mol) acrylic acid and 119.48 g methanol were used to obtain 238.96 g of a 50% active solution of N-dodecyl-N'-[3-(dimethylammonium)propyl]-succinic acid diamide acrylate in methanol.

Example 30: N-dodecyl-N'-[6-(dimethylammonium)hexyl]-succinic acid diamide acrylate 100 g (0.25 mol) of N-dodecyl-N'-[6-(dimethylamino)hexyl]-succinic acid diamide according to example 2, 17.50 g (0.23 mol) acrylic acid and 117.50 g methanol were used to obtain 235 g of a 50% active solution of N-dodecyl-N'-[6-(dimethylammonium)hexyl]-succinic acid diamide acrylate in methanol.

Example 31: N-dodecyl-N'-[3-(1-piperidylium)propyl]-succinic acid diamide acrylate 100 g (0.24 mol) of N-dodecyl-N'-[3-(1-piperidyl)propyl]-succinic acid diamide according to example 12, 17.58 g (0.24 mol) acrylic acid and 117.58 g methanol were used to obtain 235.16 g of a 50% active solution of N-dodecyl-N'-[3-(1-piperidylium)propyl]-succinic acid diamide acrylate in methanol.

Example 32: N-dodecyl-N'-[3-(4-methylpiperazin-1-ylium]-succinic acid diamide acrylate 100 g (0.23 mol) of N-dodecyl-N'-[3-(4-methylpiperazin-1-yl]-succinic acid diamide according to example 13, 16.56 g (0.23 mol) acrylic acid and 116.56 g methanol were used to obtain 233.12 g of a 50% active solution of N-dodecyl-N'-[3-(4-methylpiperazin-1-ylium]-succinic acid diamide acrylate in methanol.

Example 33: N-dodecyl-N'-[3-(dibutylammonium)propyl]-phthalic acid diamide acrylate 100 g (0.20 mol) of N-dodecyl-N'-[3-(dibutylamino)propyl]-phthalic acid diamide according to example 11, 14.40 g (0.20 mol) acrylic acid and 114.40 g methanol were used to obtain 228.8 g of a 50% active solution of N-dodecyl-N'-[3-(dibutylammonium)propyl]-phthalic acid diamide acrylate in methanol.

Example 34: N-dodecyl-N-methyl-N'-[3-(dibutylammonium)propyl]-succinic acid diamide acrylate 100 g (0.21 mol) of N-dodecyl-N-methyl-N'-[3-(dibutylamino)propyl]-succinic acid diamide according to example 14, 15.39 g (0.21 mol) acrylic acid and 115.39 g methanol were used to obtain 130.78 g of a 50% active solution of N-dodecyl-N-methyl-N'-[3-(dibutylammonium)propyl]-succinic acid diamide acrylate in methanol.

Example 35: N-dodecyl-N'-[3-(dibutylammonium)propyl]-malonic acid diamide acrylate 100 g (0.22 mol) of N-dodecyl-N'-[3-(dibutylamino)propyl]-malonic acid diamide according to example 15, 16.37 g (0.22 mol) acrylic acid and 116.37 g methanol were used to obtain 232.74 g of a 50% active solution of N-dodecyl-N'-[3-(dibutylammonium)propyl]-malonic acid diamide acrylate in methanol.

TABLE 1

Characterization of inhibitors tested

| Example | R | A | B | $R^1$ | $R^2$ | $R^3$ | $R^4$ | $R^5$ | $M^-$ |
|---|---|---|---|---|---|---|---|---|---|
| 17 | $C_{12}H_{25}$ | $C_2H_4$ | $C_3H_6$ | H | $C_4H_9$ | $C_4H_9$ | H | H | acrylate |
| 18 | $C_{12}H_{25}$ | $C_2H_4$ | $C_3H_6$ | H | $C_4H_9$ | $C_4H_9$ | H | H | acetate |
| 19 | $C_{12}H_{25}$ | $C_2H_4$ | $C_3H_6$ | H | $C_4H_9$ | $C_4H_9$ | H | H | dodecanoate |
| 20 | $C_{12}H_{25}$ | $C_2H_4$ | $C_3H_6$ | H | $C_4H_9$ | $C_4H_9$ | H | H | cocoate |
| 21 | $C_8H_{17}$—$C_{18}H_{37}$ | $C_2H_4$ | $C_3H_6$ | H | $C_4H_9$ | $C_4H_9$ | H | H | acrylate |
| 22 | $C_{12}H_{25}$ | $C_2H_4$ | $C_3H_6$ | H | $C_4H_9$ | $C_4H_9$ | H | H | acrylate |
| 23 | $C_{12}H_{25}$ | CH(OH)—$CH_2$ | $C_3H_6$ | H | $C_4H_9$ | $C_4H_9$ | H | H | acrylate |
| 24 | $C_8H_{17}$—$C_{18}H_{37}$ | CH(OH)—$CH_2$ | $C_3H_6$ | H | $C_4H_9$ | $C_4H_9$ | H | H | acrylate |
| 25 | $C_{12}H_{25}$ | CH(OH)—CH(OH) | $C_3H_6$ | H | $C_4H_9$ | $C_4H_9$ | H | H | acrylate |
| 26 | $C_8H_{17}$—$C_{18}H_{37}$ | CH(OH)—CH(OH) | $C_3H_6$ | H | $C_4H_9$ | $C_4H_9$ | H | H | acrylate |
| 27 | $C_{12}H_{25}$ | $C_2H_4$ | $C_4H_8$ | H | $C_4H_9$ | $C_4H_9$ | H | H | acrylate |
| 28 | $C_{12}H_{25}$ | $C_2H_4$ | $C_2H_4$ | H | $C_4H_9$ | $C_4H_9$ | H | H | acrylate |
| 29 | $C_{12}H_{25}$ | $C_2H_4$ | $C_3H_6$ | H | $CH_3$ | $CH_3$ | H | H | acrylate |
| 30 | $C_{12}H_{25}$ | $C_2H_4$ | $C_6H_{12}$ | H | $CH_3$ | $CH_3$ | H | H | acrylate |
| 31 | $C_{12}H_{25}$ | $C_2H_4$ | $C_3H_6$ | H | 1-piperidyl | | H | H | acrylate |
| 32 | $C_{12}H_{25}$ | $C_2H_4$ | $C_3H_6$ | H | 4-methyl-piperazin-1-yl | | H | H | acrylate |
| 33 | $C_{12}H_{25}$ | $C_6H_4$ | $C_3H_6$ | $CH_3$ | $C_4H_9$ | $C_4H_9$ | H | H | acrylate |
| 34 | $C_{12}H_{25}$ | $C_2H_4$ | $C_3H_6$ | $CH_3$ | $C_4H_9$ | $C_4H_9$ | H | H | acrylate |
| 35 | $C_{12}H_{25}$ | $CH_2$ | $C_3H_6$ | H | $C_4H_9$ | $C_4H_9$ | H | H | acrylate |

To evaluate the performance of the presently disclosed N-alkyl-N'—(N'',N''-dialkylammoniumalkyl)dicarboxylic acid diamide salts (I) as low dose gas hydrate inhibitors, a rocking cell test was used. The rocking cell test is a commonly used test in the art for assessing the performance of anti-agglomerant chemistry. Briefly, additives are evaluated based on their ability to effectively minimize the size of hydrate particle agglomerates and then to disperse those particles into the hydrocarbon phase. The results were classified as "pass" or "fail" based on whether hydrate blockages were detected. Performance was evaluated by determining the minimum effective dose (MED) required to register as a "pass" in the rocking cell test. The effective dosages (MEDs) were screened for 5.0 wt % NaCl brine at 50 respectively 60 vol.-% watercut and 138 bar at 4° C.

The rocking cell apparatus ("rack") is comprised of a plurality of sapphire tubes, each placed within a stainless steel support cage. Each assembled sapphire tube and steel cage (hereby referred to as a rocking cell) is typically loaded with fluids containing a hydrocarbon fluid phase and a brine phase, along with a stainless steel ball for mixing. The rocking cell can withstand pressures of up to 200 bar (2900 psi). The rocking cell, once loaded with the fluids, is then mounted on the rack with gas injection and pressure monitoring. During testing, as the gases cooled and hydrates formed, the consumed gas was substituted via a high-pressure syringe pump to maintain the system at constant pressure.

The rack was loaded with 10 rocking cells in a 2×5 configuration (two cells wide and 5 cells tall). The center position on the rack (between both cells) was fixed and allowed to rotate while the outer positions on the rack were moved vertically up and down. This vertical motion allowed the rocking cells to rotate into a positive or negative angle position. The steel ball placed inside the sapphire tube moved from one end of the cell to the other during a rocking motion. The rack rocked up and down at a rate of about 5 complete cycles (up and down) every minute. The rack was further contained within a temperature controlled bath attached to a chiller with temperature control from −10° C. to 60° C.

The rocking cells were filled with three components: hydrocarbon, aqueous phase, and gas. First, each rocking sapphire tube was filled with 5 ml of dodecane and a 5 ml of 5% NaCl brine (watercut 50 vol.-%) respectively 4 ml of dodecane and 6 ml of 5% NaCl brine (watercut 60 vol.-%) for a total liquid loading of 50% total tube volume (20 mL total). The inhibitor was added as a 50 wt.-% active solution at dose rates in percent, by volume of water (vol.-%). Green Canyon gas was used for this testing with its composition given in Table 2.

TABLE 2

Green Canyon gas composition

| Component Name | Chemical Symbol | Amount (mol-%) |
|---|---|---|
| Nitrogen | $N_2$ | 0.14 |
| Carbon Dioxide | $CO_2$ | 0 |
| Methane | $C_1$ | 87.56 |
| Ethane | $C_2$ | 7.6 |
| Propane | $C_3$ | 3 |
| i-Butane | $i\text{-}C_4$ | 0.5 |
| n-Butane | $n\text{-}C_4$ | 0.8 |
| i-Pentane | $i\text{-}C_5$ | 0.2 |
| n-Pentane | $n\text{-}C_5$ | 0.2 |

Rocking Cell Test Procedure:

A. Pretest Steps: Once the rack has been loaded with the rocking cells containing hydrocarbon fluid and brine, the rocking cells are evacuated with a vacuum pump for 15-20 minutes. While evacuating, the bath temperature is increased to the starting test temperature of 49° C. Once the bath has reached 49° C., the cells and the syringe pump are pressurized with Green Canyon gas to 138 bar and the syringe pump is switched on to maintain pressure during initial saturation.

B. Saturation Step: The apparatus is set to rock at 5 rocks per minute for 2 hours to ensure the hydrocarbon fluids and brine loaded in the cell have been saturated with gas. This testing is performed at constant pressure and the syringe pump remains switched on and set at 138 bar for the remainder of the test.

C: Cooling Step: While maintaining a rocking rate of 5 rocks per minute, the system is cooled from 49° C. to 4° C. over 6 hours.

D. Steady State Mixing Step before Shut-in: At the constant temperature of 4° C., the apparatus is kept rocking at 5 rocks per minute for 12 hours to ensure complete hydrate formation.

E. Shut-in Step: The apparatus is set to stop rocking and to set the cell position to horizontal and kept at a constant temperature of 4° C. for 12 hours.

F. Steady State Mixing Step after Shut-in: At the conclusion of the shut in period, the apparatus is restarted at the rate of 5 rocks per minute at the constant temperature of 4° C. for 4 hours.

G. Test Completion: At the conclusion of the experiment, the apparatus is set to stop rocking and the cells are set at a negative inclination to keep fluids away from the gas injection port. The chiller bath is set to 49° C. to melt any formed hydrates and allow for depressurization and cleaning.

To determine the relative performance of each inhibitor or dose rate of inhibitor, visual observations were made during the shut in period and correlated with an interpretation of the time required for the ball within the cell to travel between two magnetic sensors. Each experiment was conducted in duplicate to confirm reproducibility. Table 2 below shows the results from some of the rocking cell tests.

For comparison the following substances according to the state of the art were tested C1: N-[3-(Dibutylammonium)propyl]-cocoylamide acrylate according to WO 2005/042675

C2: The reaction product of N-(3-Dibutylamino-propyl)-N'-octadecyl-propanamide with acrylic acid according to WO 2016/069987.

C3: N-(2-Dibutyl-2-methylammonium-ethyl)-tetrapropylenesuccinate methylsulfate according to example 5 of US 2004/163306

TABLE 3

Test results as anti-agglomerant with a water-cut of 50 vol.-%

| Test | Inhibitor | MED (vol.-%) |
|---|---|---|
| T1 | Example 17 | 0.2% |
| T2 | Example 18 | 0.4% |
| T3 | Example 19 | 0.3% |
| T4 | Example 20 | 0.3% |
| T5 | Example 21 | 0.3% |
| T6 | Example 22 | 0.6% |
| T7 | Example 23 | 0.6% |
| T8 | Example 24 | 0.6% |

TABLE 3-continued

Test results as anti-agglomerant with a water-cut of 50 vol.-%

| Test | Inhibitor | MED (vol.-%) |
|---|---|---|
| T9 | Example 25 | 0.6% |
| T10 | Example 26 | 0.6% |
| T11 | Example 27 | 0.4% |
| T12 | Example 28 | 0.4% |
| T13 | Example 29 | 0.6% |
| T14 | Example 30 | 0.6% |
| T15 | Example 31 | 0.4% |
| T16 | Example 32 | 0.5% |
| T17 | Example 33 | 0.6% |
| T18 | Example 34 | 0.4% |
| T19 | Example 35 | 0.5% |
| T20 (comp.) | Example C1 | 0.7% |
| T21 (comp.) | Example C2 | 0.8% |
| T22 (comp.) | Example C3 | 0.9% |

MED = minimum effective dose; comp. = comparative, not according to the invention.

TABLE 4

Test results as anti-agglomerant with a water-cut of 60 vol.-%

| Test | Inhibitor | MED (vol.-%) |
|---|---|---|
| T23 | Example 17 | 0.3% |
| T24 | Example 18 | 0.5% |
| T25 | Example 19 | 0.5% |
| T26 | Example 20 | 0.4% |
| T27 | Example 21 | 0.4% |
| T28 | Example 22 | 0.7% |
| T29 | Example 23 | 0.7% |
| T30 | Example 24 | 0.8% |
| T31 | Example 25 | 0.8% |
| T32 | Example 26 | 0.7% |
| T33 | Example 27 | 0.5% |
| T34 | Example 28 | 0.6% |
| T35 | Example 29 | 0.9% |
| T36 | Example 30 | 0.8% |
| T37 | Example 31 | 0.5% |
| T38 | Example 32 | 0.7% |
| T39 | Example 33 | 0.7% |
| T40 | Example 34 | 0.6% |
| T41 | Example 35 | 0.7% |
| T42 (comp.) | Example C1 | 1.1% |
| T43 (comp.) | Example C2 | 1.2% |
| T44 (comp.) | Example C3 | 1.5% |

MED = minimum effective dose; comp. = comparative, not according to the invention.

In a further set of tests the temperature was set at 4° C. and the time in hours was measured for hydrates to form under isobaric conditions using the same dose rate of 0.6 vol.-% for all products (induction time)

TABLE 5

Induction times at 4° C.

| Test | Inhibitor | Induction Time (Hours) |
|---|---|---|
| T44 | Example 17 | 20 |
| T45 | Example 18 | 12 |
| T46 | Example 19 | 12 |
| T47 | Example 20 | 15 |
| T48 | Example 21 | 16 |
| T49 | Example 22 | 12 |
| T50 | Example 23 | 10 |
| T51 | Example 24 | 12 |
| T52 | Example 25 | 12 |
| T53 | Example 26 | 10 |
| T54 | Example 27 | 12 |
| T55 | Example 28 | 12 |
| T56 | Example 29 | 9 |
| T57 | Example 30 | 10 |
| T58 | Example 31 | 13 |
| T59 | Example 32 | 10 |
| T60 | Example 33 | 12 |
| T61 | Example 34 | 15 |
| T62 | Example 35 | 18 |
| T63 (comp.) | Example C1 | 3 |
| T64 (comp.) | Example C2 | 2 |
| T65 (comp.) | Example C3 | 3 |

As can be seen from the above test results, the products according to the invention show an improved performance over the gas hydrate inhibitors according to the state of the art. They require lower dosage rates even at raised water cuts and allow for longer shut-in times.

The invention claimed is:

1. A gas hydrate inhibitor comprising an N-alkyl-N'—(N'',N''-dialkylammoniumalkyl)dicarboxylic acid diamide salt represented by the formula (I)

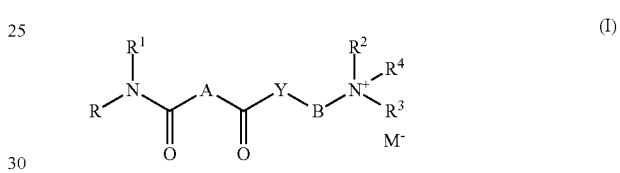

wherein
R is an alkyl or alkenyl group having from 8 to 22 carbon atoms,
$R^1$ is hydrogen, a $C_1$- to $C_{22}$ alkyl group or a $C_3$- to $C_{22}$ alkenyl group,
$R^2$ and $R^3$ are each independently an alkyl group containing 1 to 10 carbon atoms or together form an optionally substituted ring having 5 to 10 ring atoms, wherein the ring may carry up to 3 substituents,
$R^4$ is hydrogen,
A is an optionally substituted hydrocarbyl group containing from 1 to 18 carbon atoms,
B is an alkylene group having from 2 to 6 carbon atoms,
Y is $NR^5$,
$R^5$ is hydrogen, a $C_1$- to $C_{22}$ alkyl group or a $C_3$- to $C_{22}$ alkenyl group, and
M– is an anion.

2. The gas hydrate inhibitor according to claim 1 wherein $R^1$ is hydrogen or methyl.

3. The gas hydrate inhibitor according to claim 1, wherein $R^1$ is hydrogen.

4. The gas hydrate inhibitor according to claim 1, wherein $R^2$ and $R^3$ are each independently an alkyl group having 1 or 6 carbon atoms.

5. The gas hydrate inhibitor according to claim 1, wherein $R^2$ and $R^3$ are each independently an alkyl group having 4 or 5 carbon atoms.

6. The gas hydrate inhibitor according to claim 1, wherein $R^2$ and $R^3$ are each independently a linear alkyl group.

7. The gas hydrate inhibitor according to claim 1, wherein $R^2$ and $R^3$ are the same.

8. The gas hydrate inhibitor according to claim 1, wherein $R^5$ is hydrogen.

9. The gas hydrate inhibitor according to claim 1, wherein R is an alkyl or alkenyl group having from 10 to 18 carbon atoms.

10. The gas hydrate inhibitor according to claim 1, wherein A is an alkylene group having 2 to 6 carbon atoms.

11. The gas hydrate inhibitor according to claim 1, wherein A is an aromatic group having 6 to 12 carbon atoms.

12. The gas hydrate inhibitor according to claim 1, wherein B is an alkylene group having 2, 3 or 4 carbon atoms.

13. The gas hydrate inhibitor according to claim 1, wherein B is an ethylene group having the formula $CH_2$—$CH_2$— or a propylene group having the formula $CH_2$—$CH_2$—$CH_2$—.

14. The gas hydrate inhibitor according to claim 1, wherein M– is selected from the group consisting of sulfate, sulfide, carbonate, bicarbonate, nitrate, halogenides and carboxylates.

15. The gas hydrate inhibitor according to claim 1, wherein M– is a carboxylate anion.

16. The gas hydrate inhibitor according to claim 1, wherein M– is the anion of a monocarboxylic acid having 1 to 22 carbon atoms.

17. The gas hydrate inhibitor according to claim 1, wherein the gas hydrate inhibitor corresponds to formula (Ib)

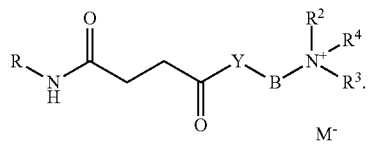
(Ib)

18. The gas hydrate inhibitor according to claim 1, wherein the gas hydrate inhibitor corresponds to formula (Ic)

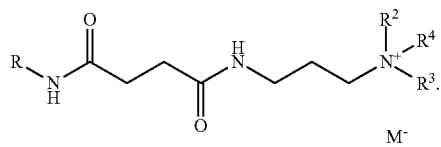
(Ic)

19. The gas hydrate inhibitor according to claim 1, wherein the gas hydrate inhibitor corresponds to formula (Id)

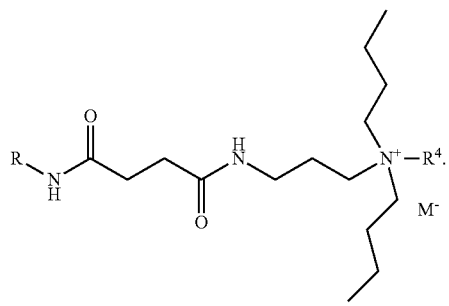
(Id)

20. The gas hydrate inhibitor according to claim 1, wherein the gas hydrate inhibitor corresponds to formula (If)

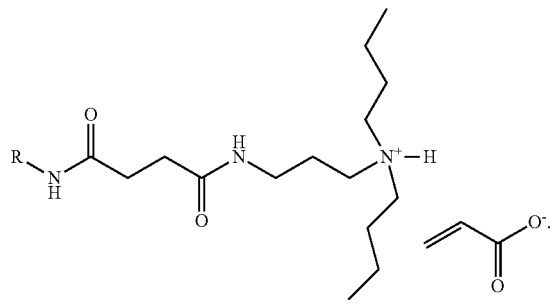
(If)

21. The gas hydrate inhibitor according to claim 1, wherein the gas hydrate inhibitor comprises both an N-alkyl-N'—(N'',N''-dialkylammoniumalkyl)dicarboxylic acid diamide salt according to formula (I)

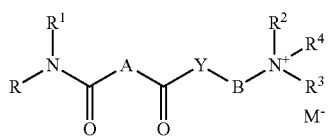
(I)

and its corresponding base which is an N-alkyl-N'—(N'', N''-dialkylaminoalkyl)dicarboxylic acid diamide according to formula (II)

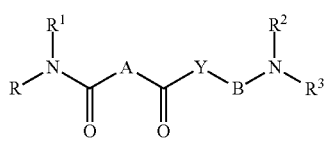
(II)

wherein
R is an alkyl or alkenyl group having from 8 to 22 carbon atoms,
$R^1$ is hydrogen, a $C_1$- to $C_{22}$ alkyl group or a $C_3$- to C22 alkenyl group,
$R^2$ and $R^3$ are each independently an alkyl group containing 1 to 10 carbon atoms or together form an optionally substituted ring having 5 to 10 ring atoms, wherein the ring may carry up to 3 substituents,
A is an optionally substituted hydrocarbyl group containing from 1 to 18 carbon atoms,
B is an alkylene group having from 2 to 6 carbon atoms,
Y is $NR^5$, and
$R^5$ is hydrogen, a $C_1$- to $C_{22}$ alkyl group or a $C_3$- to $C_{22}$ alkenyl group.

22. The gas hydrate inhibitor according to claim 1, wherein the gas hydrate inhibitor contains an organic solvent.

23. A method for inhibiting the agglomeration of gas hydrates which comprises the addition of a gas hydrate inhibitor according claim 1, to a fluid containing gas and water.

24. The method according to claim 23 wherein the dosage rate of the gas hydrate inhibitor according claim 1, is between 0.01 and 5% by volume (based on the volume of the aqueous phase).

* * * * *